United States Patent [19]

Reinehr et al.

[11] Patent Number: 4,918,215

[45] Date of Patent: Apr. 17, 1990

[54] 4-HALOGENOSTILBENE DERIVATIVES AND PROCESSES FOR THEIR PREPARATION

[75] Inventors: Dieter Reinehr, Kandern, Fed. Rep. of Germany; Alwyn Spencer, Basel, Switzerland

[73] Assignee: Ciba-Geigy Corporation, Ardsley, N.Y.

[21] Appl. No.: 657,451

[22] Filed: Oct. 3, 1984

Related U.S. Application Data

[63] Continuation of Ser. No. 360,015, Mar. 19, 1982, abandoned.

[30] Foreign Application Priority Data

Mar. 31, 1981 [CH] Switzerland ........................ 2180/81

[51] Int. Cl.$^4$ .................... C07C 121/50; C07C 69/76; C07D 303/08
[52] U.S. Cl. ..................................... 558/401; 546/255; 549/563; 560/8; 560/81; 568/325; 568/661; 570/184; 564/161
[58] Field of Search ................. 260/465 G; 560/8, 81; 546/245; 549/563; 558/401; 568/325, 661; 570/184; 564/181

[56] References Cited

U.S. PATENT DOCUMENTS

| | | | |
|---|---|---|---|
| 3,542,847 | 11/1970 | Drinkard | 260/465.9 |
| 3,869,500 | 3/1975 | Kominami et al. | 260/465.3 |
| 4,108,887 | 8/1978 | Fleck et al. | 260/465 H |
| 4,317,782 | 3/1982 | Eckstein et al. | 260/464 K X |
| 4,380,514 | 4/1983 | Seybold | 260/465 H |
| 4,440,694 | 4/1984 | Bellus et al. | 260/465 D |

FOREIGN PATENT DOCUMENTS

219035 1/1962 Austria.
920988 3/1963 United Kingdom.

*Primary Examiner*—Alan Siegel
*Attorney, Agent, or Firm*—Kevin T. Mansfield

[57] ABSTRACT

Novel compounds of the formula

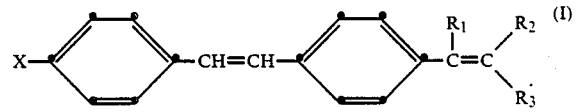

and processes for their preparation are described. X represents bromine or iodine and $R_1$, $R_2$ and $R_3$ have the meaning indicated in the patent claim. The compounds (I) are valuable intermediates for the preparation of fluorescent brighteners of the divinylstilbene type.

8 Claims, No Drawings

4-HALOGENOSTILBENE DERIVATIVES AND PROCESSES FOR THEIR PREPARATION

This application is a continuation of application Ser. No. 360,015, filed 3/19/82 now abandoned.

The invention relates to novel 4-halogenostilbene derivatives and processes for their preparation. The novel 4-halogenostilbene derivatives are available intermediates for the preparation of fluorescent brighteners of the divinylstilbene type.

Fluorescent brighteners of the divinylstilbene type are described, for example, in U.S. Pat. No. 4,108,887. However, their preparation is rather time consuming, particularly if asymmetric compounds are concerned. The starting materials required for this purpose, for example the aldehydes, are also difficult of access in some cases.

The invention relates to novel 4-halogenostilbene derivatives of the formula I

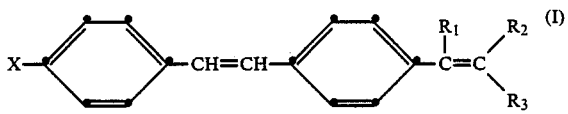

in which X represents bromine or iodine, $R_1$ represents hydrogen, alkyl or a non-chromophoric esterified carboxyl group, $R_2$ represents alkyl or alkenyl which is unsubstituted or substituted by non-chromophoric groups, or represents a non-chromophoric substituent of the second order and $R_3$ represents hydrogen or alkyl or alkenyl which is unsubstituted or substituted by non-chromophoric groups.

The compounds of the formula I can be prepared in a very simple manner and using readily accessible starting materials either (a) by reacting a compound of the formula IIa

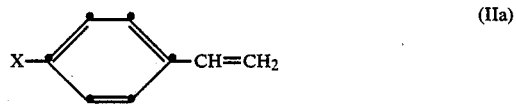

in the presence of a base and with the addition of palladium metal or palladium compounds which form phosphorus-free, labile palladium(O) compounds under the reaction conditions, as a catalyst, with a compound of the formula IIIa

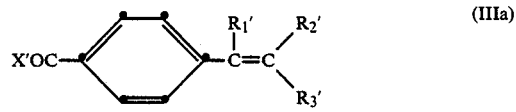

or (b) by reacting a compound of the formula IIb

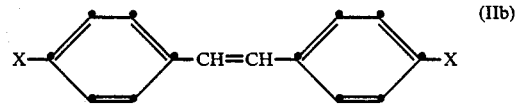

in the presence of a base, together with a palladium compound containing arsenic or phosphorus, with a compound of the formula IIIb

in which formulae X, $R_1$, $R_2$ and $R_3$ have the meaning indicated under formula I, X' represents chlorine, bromine or iodine, preferably chlorine, and $R_1'$, $R_2'$ and $R_3'$ can have the same meaning as $R_1$, $R_2$ and $R_3$, but are free from substituents capable of reacting with group X'OC—, such as —OH, —NH$_2$, —NH— or —COOH groups.

Preparation in accordance with process variant (a) is preferred.

The substituents present in the compounds of the formula I are, in general, substituents such as are customary in the field of fluorescent brighteners.

X preferably represents bromine. Alkyl groups $R_1$, $R_2$ and $R_3$ can be straight-chain or branched and preferably have 1–6 C atoms, in particular 1 or 2 C atoms. Alkenyl groups $R_2$ and $R_3$ advantageously contain 2 to 4 C atoms, preferably 3 C atoms. The following may be mentioned as examples of such alkyl and alkenyl groups: the methyl, ethyl, n-propyl, isopropyl, n-butyl, tert.-butyl, n-pentyl, n-hexyl, vinyl and allyl groups.

Examples of non-chromophoric substituents on alkyl or alkenyl groups of the type defined are alkoxy, alkoxyalkoxy, dialkylamino or alkoxycarbonyl groups, and also halogen atoms, such as fluorine or chlorine, or phenyl which is unsubstituted or substituted by non-chromophoric groups, for example phenyl which can be substituted by alkyl, alkoxy, halogen, cyano, a carboxylic acid ester or amide group or a carboxylic acid acyl radical. Alkoxy or alkyl moieties in the substituents mentioned preferably contain 1 to 4 C atoms, particularly 1 or 2 C atoms. Alkenyl groups $R_2$ and $R_3$ are preferably unsubstituted. Alkoxyalkoxy substituents advantageously have 2–6 C atoms, in particular 4–6 C atoms. Alkylene bridge members in alkoxyalkoxy substituents are advantageously ethylene, 1,2-propylene, 1,2-butylene or 2,3-butylene, but ethylene is preferred.

Non-chromophoric substituents of the second order are electron-attracting substituents which do not impart any colour to the compounds of the formula I; this would be detrimental to their use for the preparation of fluorescent brighteners. The following may be mentioned as examples: acyl radicals of organic non-chromophoric carboxylic acids, the cyano and trifluoromethyl groups and phenylalkyl or carboxylic acid ester and amide groups which are substituted or unsubstituted. Examples of the ester groups present in the molecule, particularly the non-chromophoric, esterified carboxyl groups, are carboxylic acid cycloalkyl ester groups or carboxylic acid alkyl ester groups which are unsubstituted or substituted by alkyl and in which the alkyl can be substituted by alkoxy or alkoxyalkoxy groups of the type mentioned above; also carboxylic acid phenyl ester or phenyl alkyl ester groups which are substituted or unsubstituted and in which phenyl can be substituted as indicated above.

Carboxylic acid amide groups can be substituted or unsubstituted. Only cyclic or disubstituted carboxylic acid amide groups are suitable for the process variant (a). Examples of suitable substituents are alkyl groups, alkoxyalkyl groups, dialkylaminoalkyl groups, cycloalkyl groups and phenyl or phenylalkyl groups which are substituted or unsubstituted.

Preferred compounds of the formula I are those in which X represents bromine, $R_1$ represents hydrogen, $C_{1-6}$ alkyl or —COOR‴, preferably hydrogen or $C_{1-4}$ alkyl and, in particular, hydrogen or methyl, $R_2$ represents $C_{1-6}$ alkyl which is unsubstituted or substituted by $C_{1-4}$ alkoxy or $C_{2-5}$ alkoxycarbonyl, and particularly represents $C_{2-4}$ alkenyl, —CN, —CF$_3$ or a group

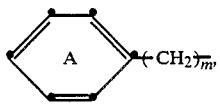

—CO—R, —CO—NR′R″ or —COOR‴, advantageously $C_{2-4}$ alkenyl and, in particular, —CN, —CONR′R″, —COOR‴ or —CO—R, especially —CN or —COOR‴, $R_3$ represents hydrogen or $C_{1-6}$ alkyl which is unsubstituted or substituted by $C_{1-4}$ alkoxy or $C_{2-5}$ alkoxycarbonyl, particularly hydrogen, $C_{1-4}$ alkyl or —CH$_2$COO—$C_{1-4}$ alkyl and, very particularly preferentially hydrogen, methyl or —CH$_2$COOCH$_3$ or —CH$_2$COOC$_2$H$_5$, R represents methyl, $C_{2-6}$ alkyl which is unsubstituted or substituted by $C_{1-4}$ alkoxy or $C_{4-6}$ alkoxyalkoxy, or represents a radical of the formula

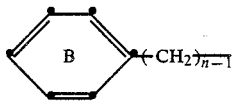

or naphthyl, particularly methyl, $C_{2-6}$ alkyl which is unsubstituted or substituted by $C_{1-4}$ alkoxy or $C_{4-6}$ alkoxyalkoxy, the radical of the formula

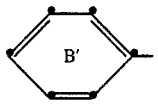

or naphthyl and very particularly phenyl which is unsubstituted or monosubstituted by chlorine, methyl or methoxy, or unsubstituted $C_{1-6}$ alkyl, preferably $C_{1-4}$ alkyl and, in particular, methyl, R′ represents hydrogen, methyl, $C_{2-6}$ alkyl which is unsubstituted or substituted by $C_{1-4}$ alkoxy, $C_{4-6}$ alkoxyalkoxy or di-($C_{1-4}$ alkyl)-amino, cyclohexyl which is unsubstituted or substituted by methyl or ethyl, or a radical of the formula

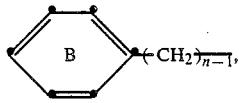

particularly methyl or ethyl, or, together with R″, represents —(CH$_2$)$_4$— or —(CH$_2$)$_5$—, R″ represents hydrogen, methyl or $C_{2-6}$ alkyl which is unsubstituted or substituted by $C_{1-4}$ alkoxy or $C_{4-6}$ alkoxyalkoxy, preferably methyl or ethyl, or, together with R′, represents —(CH$_2$)$_4$— or —(CH$_2$)$_5$—, R‴ represents methyl, $C_{2-6}$ alkyl which is unsubstituted or substituted by $C_{1-4}$ alkoxy or $C_{3-6}$ alkoxyalkoxy, cyclohexyl which is unsubstituted or substituted by methyl and/or ethyl, or a radical of the formula

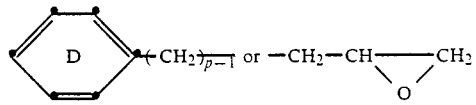

and particularly methyl or $C_{2-6}$ alkyl which is unsubstituted or substituted by $C_{1-4}$ alkoxy or $C_{3-6}$ alkoxyalkoxy, in particular alkyl havinng 1-6 C atoms and, in particular, 1-4 C atoms, and very particularly methyl or ethyl, m represents the number 1 or 2, preferably 1, and n and p independently of one another represent the number 1, 2 or 3, preferably 2 and particularly 1.

In these definitions, at least one of $R_1$ and $R_3$ preferably represents hydrogen and the aromatic rings A, B and D can be monosubstituted or disubstituted by $C_{1-3}$ alkyl and/or halogen, particularly chlorine. If n and p each represent the number 1, the aromatic rings B and D can be unsubstituted or trisubstituted by $C_{1-3}$ alkyl and/or halogen or monosubstituted or disubstituted by $C_{1-3}$ alkoxy. The ring B′ is unsubstituted or is substituted by halogen, particularly chlorine, $C_{1-3}$ alkyl and/or $C_{1-3}$ alkoxy. The rings mentioned are preferably unsubstituted. R′ and R″ preferably have the same meaning or together represent —(CH$_2$)$_4$— or —(CH$_2$)$_5$—.

Compounds of the formula I which are also preferred are those in which X represents bromine, $R_1$ represents hydrogen or $C_{1-4}$ alkyl, $R_2$ represents $C_{2-4}$ alkenyl, —CN, —CONR′R″, —COOR‴ or —CO—R and $R_3$ represents hydrogen, $C_{1-4}$ alkyl or —CH$_2$COO—$C_{1-4}$ alkyl, at least one of $R_1$ and $R_3$ representing hydrogen and R, R′, R″ and R‴ having the meaning indicated above. R preferably represents $C_{1-6}$ alkyl or phenyl which is unsubstituted or substituted by halogen, particularly chlorine, $C_{1-3}$ alkyl or $C_{1-3}$ alkoxy, in particular unsubstituted $C_{1-4}$ alkyl or phenyl which is unsubstituted or monosubstituted by chlorine, methyl or methoxy. R′ and R″ each preferably represent methyl or ethyl or together represent —(CH$_2$)$_5$—. R‴ preferably represents methyl or $C_{2-6}$ alkyl which is unsubstituted or substituted by $C_{1-4}$ alkoxy or $C_{3-6}$ alkoxyalkoxy, in particular unsubstituted $C_{1-4}$ alkyl.

Compounds of the formula I which are particularly preferred are those in which X represents bromine, $R_1$ represents methyl and, in particular, hydrogen, $R_2$ represents —CN,

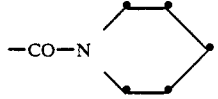

or —COOR‴, R‴ represents unsubstituted $C_{1-4}$ alkyl, in particular methyl or ethyl, and $R_3$ represents hyrogen, methyl, —CH$_2$COOCH$_3$ or —CH$_2$COOC$_2$H$_5$, at least one of $R_1$ and $R_3$ representing hydrogen.

Compounds of the formula I which are of very particular interest are those in which X represents bromine, $R_1$ and $R_3$ represent hydrogen and $R_2$ represents —CN or —COOC$_2$H$_5$.

The catalysts and the compounds of the formulae IIa, IIb, IIIa and IIIb are known or can be prepared in a manner which is known per se.

The invention also relates to certain novel starting materials of the formula IIIa, namely the compounds of the formulae

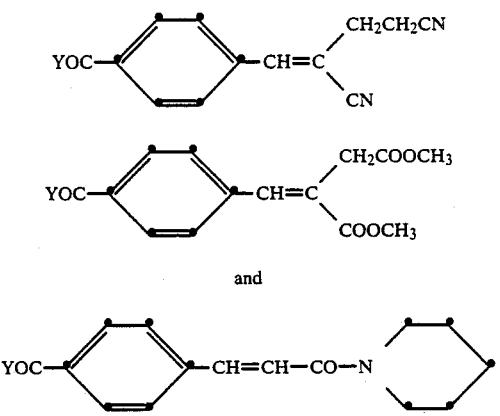

in which Y represents —OH or —Cl. These were developed specially for the preparation of the compounds, according to the invention, of the formula I.

As far as the preparation of compounds of the formula IIIb is concerned, cf. for example, Houben-Weyl, volume 5/1b (1972). The compounds of the formula IIIa can be prepared, for example, by reacting 4-bromobenzoic acid with compounds HC(R$_1$)=C(R$_2$)(R$_3$) as specified in J. Org. Chem. 42, 3903 (1977) and by subsequently converting the reaction produce into acid halides of the type defined.

The compounds of the formula IIa and IIIa or IIb and IIIb, respectively, are generally employed in stoichiometric quantities. However, it is also possible to use an excess of the compound of the formula IIa or IIb, for example an excess which is not more than about 5-molar of the compound of the formula IIa or IIb.

Besides palladium metal, the palladium compounds of the type define which are employed for the reaction according to process variant (a) can be, for example, compounds of the formula IV $$M^y[PdL_{n1}]^x \qquad (IV)$$

in which n$_1$ represents an integer from 2 to 4, x represents 2⊕ to 2⊖, y represents —(x), M represents a counter-ion if x is not 0, and the Ls represent identical or different phosphorus-free ligands, for example Cl, Br, I, —CN, —NO$_3$, C$_{1-12}$ alkyl—COO,

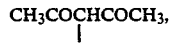

NH$_3$, 2,2'-bipyridyl, o-phenanthroline,

or —NC-phenyl. Examples of suitable compounds of the formula IV are PdCl$_2$, PdBr$_2$, Pd(CN)$_2$, Pd(NO$_3$)$_2$, Pd(O$_2$C—C$_{1-12}$ alkyl)$_2$, especially Pd(OOCCH$_3$)$_2$,

[Pd(NH$_3$)$_4$]Cl$_2$, [PdCl$_4$]Na$_2$, Pd(OOCCH$_3$)$_2$(2,2'-bipyridyl), Pd(OOCCH$_3$)$_2$-(o-phenanthroline),

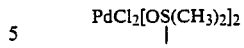

and PdCl$_2$(NC-phenyl)$_2$.

In addition to the compounds mentioned above, it is also possible to employ palladium compounds of other stages of oxidation for the process variant (a), for example bis-(dibenzylideneacetone)-palladium(O) and bis-(isonitrile)-palladium(O) compounds. The following may be mentioned as examples of such isonitriles: bis-(cyclohexyl isonitrile)-palladium(O), bis-(isopropyl isonitrile)-palladium (O), bis-(tert.-butyl isonitrile)-palladium(O), bis-(p-tolyl isonitrile)-palladium(O), bis-(phenyl isonitrile)-palladium(O) and bis-(p-methoxyphenyl isonitrile)-palladium(O). Of these, bis-(dibenzylideneacetone)-palladium(O), bis-(cyclohexyl isonitrile)-palladium(O) and bis-(isopropyl isonitrile)-palladium(O) are preferred.

The catalysts which are employed for the reaction according to process variant (b) can be, for example, palladium complexes of the type described in U.S. Pat. No. 3,922,299, above all complexes of Pd(OOC—C$_{1-12}$ alkyl)$_2$, particularly palladium acetate, with trivalent phosphorus or arsenic compounds, such as trialkylphosphines, triarylphosphines, trialkoxyphosphines, triphenoxyphosphines or trihalogenophosphines or trialkylarsines, triarylarsines, trialkoxyarsines, triphenoxyarsines or trihalogenoarsines, or mixtures of substituted trivalent phosphorus or arsenic compounds. The following may be mentioned as examples of such phosphorus or arsenic compounds: triphenylarsine, diphenylmethylphosphine, diphenylmethoxyphospine, trimethylphosphine, triethylphosphine, tri-n-butylphosphine, triphenylphosphine, phenyldi-n-butoxyphosphine, phosphorus trichloride, phenyldichlorophosphine and tri-o-tolylphosphine. The said complexes can be employed as such or can be formed in situ, ie. in the reaction medium. It is particularly preferable to use a mixture of palladium acetate and triphenylphosphine or tri-o-tolylphosphine.

The catalysts used in the method (a) of preparation are preferably PdCl$_2$, PdBr$_2$, Pd(OOCCH$_3$)$_2$,

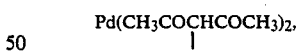

Pd(OOCCH$_3$)$_2$(2,2'-bipyridyl), PdCl$_2$(NC-phenyl)$_2$, bis-(dibenzylideneacetone)-palladium(O) and bis-(cyclohexyl isonitrile)-palladium(O). PdCl$_2$, palladium acetate and bis-(dibenzylideneacetone)-palladium(O) are very particularly preferred. Catalysts which are preferred for the method (b) of preparation are mixtures of palladium acetate and triphenylphosphine or tri-o-tolylphosphine.

In general, the catalysts are employed in an amount of 0.0001 to 20 mol%, preferably about 0.001 to 3 mol%, relative to the compound of the formula IIa or IIb.

The bases used in the process according to the invention can be either inorganic compounds or organic compounds which are adequately soluble in the reaction medium. Examples of suitable bases are compounds of the formulae V to VII $$(Z')^{n\oplus}(\ominus OOCQ')_{m_1}, \quad (V)$$

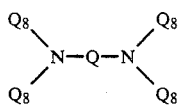
(VI)

or

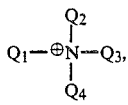
(VII)

and also cyclic tertiary amines, for example N-methylpiperidine, N-ethylpiperidine, 1,2,2,6,6-pentamethylpiperidine, 4-oxo-1,2,2,6,6-pentamethylpiperidine, 1,4-diazabicyclo[2,2,2]octane (DABCO), N-alkylmorpholines and N-alkylpyrrolidines, such as N-methylmorpholine, N-ethylmorpholine, N-methylpyrrolidine and N-ethylpyrrolidine, or N,N'-dialkylpiperazines, such as N,N'-dimethylpiperazine.

In the above formulae, $m_1$ represents the number 1 or 2, Q' represents phenyl or $C_{1-17}$ alkyl, Z' represents an alkali metal cation, an alkaline earth metal cation or $$Q_1 - \overset{Q_2}{\underset{Q_4}{\overset{|}{\oplus N}}} - Q_3,$$

Q represents straight-chain or branched alkylene having 2–6 C atoms, $Q_1$ represents hydrogen, $C_{1-12}$ alkyl, cyclopentyl, cyclohexyl, benzyl or phenyl, $Q_2$, $Q_3$ and $Q_4$ represent identical or different $C_{1-12}$ alkyl groups, $Q_5$ represents $C_{1-12}$ alkyl, cyclopentyl, cyclohexyl, phenyl or benzyl which can also be substituted, for example by a halogen atom, such as chlorine or bromine, or an alkyl or alkoxy group, each of which has 1–4, particularly 1 or 2, C atoms, $Q_6$ and $Q_7$ represent identical or different $C_{1-12}$ alkyl groups and $Q_8$ represents methyl or ethyl.

When Z' represents an alkali metal cation this is especially the sodium cation and, in particular, the lithium cation. Alkyl groups Q' and $Q_1$ to $Q_7$ can be straight-chain or branched. If $Q_5$ to $Q_7$ represent alkyl groups, these alkyl groups advantageously contain a total of at least 9 C atoms, while alkyl groups $Q_1$ to $Q_4$ preferably contain 1–4 C atoms each. The following are examples of compounds of the formulae V to VII: lithium acetate, butyrate and stearate, barium acetate, calcium acetate, potassium stearate, calcium stearate, sodium stearate, lithium benzoate and sodium benzoate and also the corresponding trimethylammonium, tetramethylammonium, tetraethylammonium and tetra-n-butylammonium salts; triethylamine, tri-n-butylamine, tri-(2-ethylhexylamine), tri-n-octylamine and tri-n-dodecylamine; N-benzyldialkylamines, such as N-benzyldimethylamine, N-benzyldiethylamine, N-(4-chlorobenzyl)-dimethylamine, N-(3-methylbenzyl)-dimethylamine and N-(3-methoxybenzyl)-dimethylamine; N,N,N',N'-tetramethylethylenediamine, N,N,N',N'-tetraethylethylenediamine, N,N,N',N'-tetramethyl-1,3-diaminopropane and N,N,N',N'-tetramethyl-1,6-diaminohexane. Other inorganic bases, in particular water-soluble bases, such as alkali metal carbonates or bicarbonates, are also suitable for the method (b) of preparation.

It is preferable to use, as bases, tertiary amines of the type mentioned above, in particular N-ethylmorpholine or compound of the formula VI in which $Q_5$ represents 4-chlorobenzyl, 4-methylbenzyl or 4-methoxybenzyl and, in particular, benzyl and $Q_6$ and $Q_7$ each represent alkyl having 1–4 C atoms, in particular 1 or 2 C atoms, or in which $Q_5$, $Q_6$ and $Q_7$ each represent alkyl having 3–12 C atoms. N-Benzyldimethylamine, N-ethylmorpholine and tri-n-butylamine are particularly preferred.

The reaction temperatures for the reaction according to the invention are advantageously between 0° and 200° C., preferably between 90° and 150° C.

If the compounds of the formula IIa or IIb are liquid, the reaction can be carried out without adding a solvent. However, the reaction is preferably carried out in an organic solvent which is inert towards the reactants. Examples of suitable inert organic solvents are aliphatic, cycloaliphatic or aromatic hydrocarbons, which can be substituted by chlorine, such as n-pentane, n-heptane, n-octane, cyclopentane, cyclohexane, benzene, toluene, xylenes and chlorobenzene; aromatic, aliphatic and cyclic ethers, such as anisole, diethyl ether, disopropyl ether, tetrahydrofuran and dioxane; nitriles, particularly benzonitrile and alkyl nitriles having 2 to 5 C atoms, such as acetonitrile, propionitrile and butyronitrile; 3-methoxypropionitrile and 3-ethoxypropionitrile; N,N-dialkylamides of aliphatic monocarboxylic acids having 1 to 3 C atoms in the acid moiety, such as N,N-dimethylformamide and N,N-dimethylacetamide; alcohols having not more than 8 C atoms, such as ethanol, propanol and tert.-butanol; aliphatic and cycloaliphatic ketones, such as acetone, diethyl ketone, methyl isopropyl ketone, cyclopentanone and cyclohexanone; esters, such as esters of carbonic acid, for example diethyl carbonate, and alkyl or alkoxyalkyl esters of aliphatic monocarboxylic acids having a total of 2 to 8 C atoms, such as methyl, ethyl, n-butyl and isobutyl acetate, ethyl and n-butyl butyrate, and 1-acetoxy-2-methoxyethane. Depending on the method of preparation, preferred solvents are nitriles, ketones, esters, cyclic ethers and aromatic hydrocarbons of the type mentioned above. Polar solvents, in particular, such as nitriles, ketones and esters, are suitable for the reaction in the presence of inorganic bases. It is very particularly preferred to carry out the reaction in the presence of an organic base and an aromatic ether or hydrocarbon, in particular anisole, xylenes or toluene. The reaction can also be carried out in a two-phase system, for example in a mixture of water and a water-immiscible solvent, such as water together with chlorobenzene, xylenes or toluene.

As already mentioned, the compounds of the formula I are valuable intermediates for the preparation of fluorescent brighteners, particularly asymmetric divinylstilbene brighteners. Brighteners of this type can be obtained, for example, by reacting a compound of the formula I, under the same reaction conditions as those described above for the process variant (b), with a compound of the formula IIIb, and it is also possible for this compound of the formula IIIb to be different from the compound employed for the reaction with compounds of the formula IIb.

EXAMPLE 1

14.83 g (50 mmols) of the acid chloride of the formula

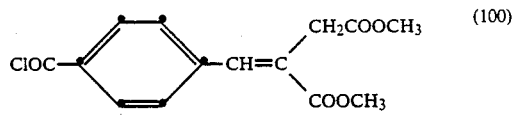

(100)

10.17 g (50 mmols) of 4-bromostyrene, 6.76 g (50 mmols) of N-benzyldimethylamine and 0.1122 g (0.5 mmol) of palladium acetate are added under argon to 100 ml of p-xylene. The reaction mixture is stirred for 2 hours at 130° C. and is then extracted by shaking with twice 50 ml of 2N HCl and with twice 50 ml of 2N NaOH, and is dried over magnesium sulfate and evaporated. Recrystallisation from cyclohexane gives 10.5 g (51% of theory) of the compound of the formula

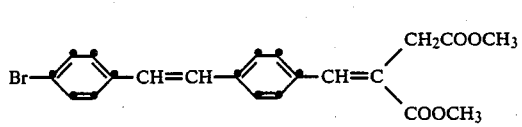

(101)

in the form of pale yellow crystals; melting point 133.3° C.

The acid chloride of the formula (100) and the corresponding free acid are novel and can be prepared as follows: 25.15 g (125 mmols) of 4-bromobenzoic acid, 24.7 g (156.25 mmols) of dimethyl itaconate, 26.55 g (262.5 mmols) of triethylamine, 0.280 g (1.25 mmmols) of palladium acetate and 1.52 g (5 mmols) of tri-o-tolylphosphine are stirred at 100° C. for 3.5 hours. The reaction mixture is poured into 150 ml of 2N HCl and the crude product is filtered off and recrystallised from toluene. This gives 25.8 g (74% of theory) of the compound of the formula

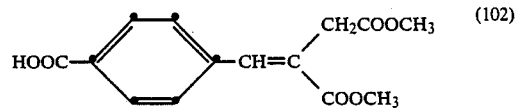

(102)

in the form of white crystals; melting point 147.0° C.

30.2 g (109 mmols) of the compound (102), 16.17 g (136.25 mmols) of thionyl chloride, 200 ml of toluene and 0.25 ml of N,N-dimethylformamide are stirred at 20° C. for 3 hours. The reaction mixture is evaporated and the residue is recrystallised from cyclohexane. This gives 29.5 g (91% of theory) of the compound (100) in the form of yellow crystals; melting point 81.0° C.

EXAMPLE 2

3.7 g (15 mmols) of stilbene-4-carboxylic acid chloride, 3.05 g (15 mmols) of 4-bromostyrene, 2.03 g (15 mmols) of N-benzyldimethylamine and 0.0336 g (0.15 mmol) of palladium acetate are added under argon to 30 ml of p-xylene. The reaction mixture is stirred at 130° C. for 1 hour. Working up as described in Example 1 gives 3.2 g (59% of theory) of the compound of the formula

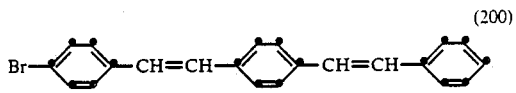

(200)

in the form of green-yellow crystals; melting point 283.7° C.

Stilbene-4-carboxylic acid chloride can be prepared as follows: 25.15 g (125 mmols) of 4-bromobenzoic acid, 16.25 g (156.25 mmols) of styrene, 26.55 g (262.5 mmols) of triethylamine, 0.28 g (1.25 mmols) of palladium acetate and 1.52 g (5 mmols) of tri-o-tolylphosphine are stirred at 100° C. for 3.5 hours. The reaction mixture is poured into 100 ml of 2N HCl and the crude product is filtered off and recrystallised from tetrahydrofuran/toluene. 15.3 g (55% of theory) of stilbene-4-carboxylic acid are obtained in the form of white crystals; melting point 252.4° C.

15.1 g (67.4 mmols) of stilbene-4-carboxylic acid, 10.0 g (84.25 mmols) of thionyl chloride, 150 ml of toluene and 0.18 ml of N,N-dimethylformamide are stirred at 70° C. for 3 hours. The reaction mixture is then evaporated and the crude product is recrystallised from n-hexane/cyclohexane. 13.7 g (84% of theory) of stilbene-4-carboxylic acid chloride are obtained in the form of white crystals; melting point 131.2° C.

EXAMPLE 3

Ethyl 4-bromostilbene-4'-acrylate. 25.8 g (0.1 mol) of 4,4'-dibromostilbene, 10 g (0.1 mol) of ethyl acrylate, 18.5 g (0.1 mol) of tri-n-butylamine, 0.224 g (0.001 mol) of palladium acetate and 0.6 g (0.002 mol) of tri-o-tolylphosphine are added under argon to 50 ml of p-xylene. The reaction mixture is stirred at 90° C. for 4 hours. Working up gives 2 g (6% of theory) of ethyl 4-bromostilbene-4'-acrylate. Melting point 166.9° C.

EXAMPLE 4

4-Bromostilbene-4'-acrylonitrile. 6.76 g (0.02 mol) of 4,4'-dibromostilbene, 1.06 g (0.02 mol) of acrylonitrile, 4.08 g (0.022 mol) of tri-n-butylamine, 0.0898 g (0.4 mmol) of palladium acetate and 0.2098 g (0.8 mmol) of triphenylphosphine are added under argon to 10 ml of toluene. The reaction mixture is stirred at 100°–115° C. for 7 hours. Working up gives 1 g (16% of theory) of 4-bromostilbene-4'-acrylonitrile in the form of a pale yellow powder. Melting point 258° C.

EXAMPLE 5

7.5 g (27 mmols) of the acid chloride of the formula

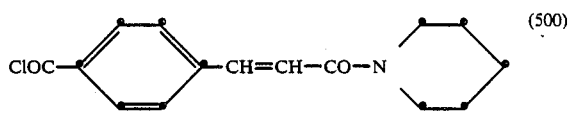

(500)

5.45 g (27 mmols) of 4-bromostyrene, 3.62 g (27 mmols) of N-benzyldimethylamine and 0.0604 g (0.27 mmol) of palladium acetate are added under argon to 70 ml of p-xylene. The reaction mixture is stirred at 130° C. for 1.5 hours. The crude product which has been precipitated is then filtered off at room temperature. Recrystallisation from carbon tetrachloride/n-hexane gives 2.1 g (20% of theory) of the compound of the formula

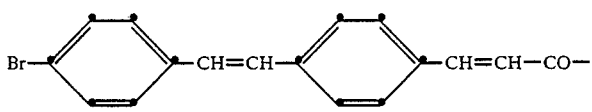 

(501)

in the form of pale green-yellow crystals; melting point 214.9° C.

The acid chloride of the formula (500) and the corresponding free acid are novel and can be prepared as follows: 20.12 g (0.1 mol) of 4-bromobenzoic acid, 17.38 g (125 mmols) of acrylic acid piperidide, 25.28 g (250 mmols) of triethylamine, 0.224 g (1 mmol) of palladium acetate and 1.216 g (4 mmols) of tri-o-tolylphosphine are stirred at 115° C. for 15 minutes. The mixture is stirred with 300 ml of 2N hydrochloric acid and the crude product is filtered off. It is dissolved in 200 ml of 2N sodium hydroxide solution and the solution is filtered. 26 ml of 10N hydrochloric acid are added to the filtrate. The precipitate is filtered off, washed with water and dried. 25.27 g (98% of theory) of 4-carboxycinnamic acid piperidide are obtained in the form of white crystals; melting point 257.1° C.

21.43 g (82.7 mmols) of the above compound, 7.52 ml (103.4 mmols) of thionyl chloride, 120 ml of toluene and 0.3 ml of N,N-dimethylformamide are stirred at 80°–100° C. for 2 hours. The reaction mixture is evaporated and the residue is recrystallised from n-hexane. 7.51 g (33% of theory) of the compound of the formula (500) are obtained in the form of yellow crystals; melting point 105° C.

EXAMPLE 6

4.77 g (20 mmols) of ethyl 4-chloroformylcinnamate, 4.04 g (20 mmols) of 4-bromostyrene, 2.72 g (20 mmols) of N-benzyldimethylamine and 0.0448 g (0.2 mmol) of palladium acetate are added under argon to 50 ml of p-xylene, and the reaction mixture is stirred at 130° C. for 1.5 hours. The product which has been precipitated is filtered off at room temperature and is then recrystallised from methanol. 0.73 g (10% of theory) of ethyl 4-bromostilbene-4'-acrylate is obtained in the form of yellow crystals; melting point 166.9° C.

The ethyl 4-chloroformylcinnamate can be prepared as follows: 10.05 g (50 mmols) of 4-bromobenzoic acid, 6.25 g (62.5 mmols) of ethyl acrylate, 12.6 g (125 mmols) of triethylamine, 0.1122 g (0.5 mmol) of palladium acetate and 0.608 g (2 mmols) of tri-o-tolylphosphine in 20 ml of toluene are boiled under reflux for 1.5 hours. The reaction mixture is extracted by shaking with 200 ml of 2N hydrochloric acid, and the crude product is filtered off and recrystallised from toluene. 10.1 g (92% of theory) of ethyl 4-carboxycinnamate are obtained in the form of white crystals; melting point 196°–197° C.

14.8 g (67 mmols) of ethyl 4-carboxycinnamate, 9.57 g (80 mmols) of thionyl chloride, 100 ml of toluene and 0.18 ml of N,N-dimethylformamide are boiled under reflux for 30 minutes. The reaction mixture is evaporated and the crude product is recrystallised from n-hexane. 12.6 g (79% of theory) of ethyl 4-chloroformylcinnamate are obtained in the form of white crystals; melting point 76.8° C.

EXAMPLE 7

2.13 g (11.1 mmols) of 4-chloroformylcinnamonitrile, 2.24 g (11.1 mmols) of 4-bromostyrene, 1.51 g (11.1 mmols) of N-benzyldimethylamine and 0.0246 g (0.11 mmol) of palladium acetate are added under argon to 30 ml of p-xylene, and the reaction mixture is stirred at 130° C. for 1.5 hours. The crude product which has been precipitated is filtered off at room temperature and is recrystallised from methanol and then from carbon tetrachloride. 0.38 g (11% of theory) of 4-bromostilbene-4'-acrylonitrile are obtained; melting point 258° C.

The 4-chloroformylcinnamonitrile can be prepared as follows: 10.05 g (50 mmols) of 4-bromobenzoic acid, 3.31 g (62.5 mmols) of acrylonitrile, 12.6 g (125 mmols) of triethylamine, 0.112 g (0.5 mmol) of palladium acetate, 0.608 g (2 mmols) of tri-o-tolylphosphine and 20 ml of toluene are boiled under reflux for 6 hours. The reaction mixture is extracted by shaking with 100 ml of 2N hydrochloric acid and the crude product is filtered off and recrystallised from methanol. 3 g (35% of theory) of 4-carboxycinnamonitrile are obtained in the form of pale yellow crystals; melting point 281° C.

14.3 g (83 mmols) of 4-carboxycinnamonitrile, 11.9 g (100 mmols) of thionyl chloride, 100 ml of toluene and 0.18 ml of N,N-dimethylformamide are boiled under reflux for 15 minutes and then evaporated. Recrystallising the residue twice from carbon tetrachloride gives 7.7 g (48% of theory) of 4-chloroformylcinnamonitrile in the form of yellow crystals; melting point 161.0° C.

EXAMPLE 8

8.54 g (35 mmols) of the acid chloride of the formula

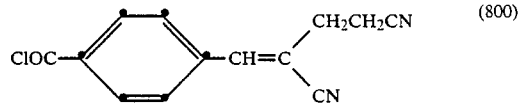

(800)

7.06 g (35 mmols) of 4-bromostyrene, 4.76 g of N-benzyldimethylamine and 0.0784 g (0.35 mmol) of palladium acetate are added under argon to 90 ml of p-xylene. The reaction mixture is stirred at 130° C. for 4.5 hours. The crude product is filtered off at room temperature and is washed with 50 ml of 2N hydrochloric acid. It is then recrystallised from ethyl methyl ketone. 3.2 g (25% of theory) of the compound of the formula

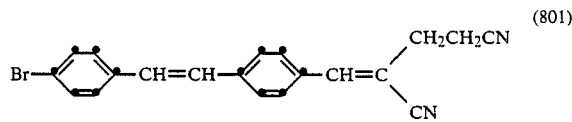

(801)

are obtained in the form of yellow-green crystals; melting point 177.2° C.

The acid chloride of the formula (800) and the corresponding free acid are novel and can be prepared as follows: 20.12 g (0.1 mol) of 4-bromobenzoic acid, 13.25 g (0.125 mol) of 2-methyleneglutarodinitrile, 21.23 g (0.21 mol) of triethylamine, 0.224 g (1 mmol) of palladium acetate, 1.216 g (4 mmols) of tri-o-tolylphosphine and 100 ml of p-xylene was stirred at 115° C. for 18 hours. The intermediate obtained (the free acid) is filtered off and washed with 100 ml of 2N hydrochloric acid. It is then dissolved in 160 ml of 2N sodium hydroxide solution and reprecipitated by adding 40 ml of 10N hydrochloric acid. After it has been filtered off and dried, 10.26 ml (0.14 mol) of thionyl chloride, 150 ml of toluene and 0.3 ml of N,N-dimethylformamide are added, and the mixture is stirred at 90° C. for 2 hours. The reaction mixture is evaporated and the crude product is recrystallised from a mixture of 125 ml of carbon tetrachloride and 35 ml of toluene. 6.24 g (26% of theory) of the compound of the formula (800) are obtained in the form of pale brown crystals; melting point 64.6° C.

What is claimed is:

1. A compound of the formula

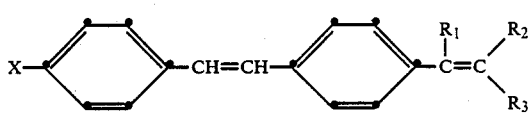

in which X represents bromine or iodine, $R_1$ represents hydrogen, alkyl or a non-chromophoric esterified carboxyl group, $R_2$ represents $C_1$–$C_6$-alkyl or $C_2$–$C_4$-alkenyl which is unsubstituted or substituted by a non-chromophoric group, or represents a non-chromophoric substituent of the second order and $R_3$ represents hydrogen or $C_1$–$C_6$-alkyl or $C_2$–$C_4$-alkenyl which is unsubstituted or substituted by a non-chromophoric group.

2. A compound of claim 1, in which X represents bromine.

3. A compound of claim 1, in which X represents bromine, $R_1$ represents hydrogen, $C_{1-6}$ alkyl or —COOR''', $R_2$ represents $C_{1-6}$ alkyl which is unsubstituted or substituted by $C_{1-4}$ alkoxy or $C_{2-5}$ alkoxycarbonyl, or represents $C_{2-4}$ alkenyl, —CN, —CF$_3$, or a group

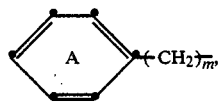

—CO—R, —CO—NR'R'' or —COOR''', $R_3$ represents hydrogen or $C_{1-6}$ alkyl which is unsubstituted or substituted by $C_{1-4}$ alkoxy or $C_{2-5}$ alkoxycarbonyl, R represents methyl, $C_{2-6}$ alkyl which is unsubstituted or substituted by $C_{1-4}$ alkoxy or $C_{4-6}$ alkoxyalkoxy, or represents a radical of the formula

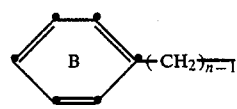

or naphthyl, R' represents hydrogen, methyl, $C_{2-6}$ alkyl which is unsubstituted or substituted by $C_{1-4}$ alkoxy, $C_{4-6}$ alkoxyalkoxy or di-($C_{1-4}$ alkyl)-amino, cyclohexyl which is unsubstituted or substituted by methyl or ethyl, or a radical of the formula

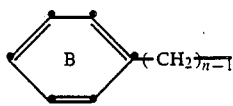

or, together with R'', represents —(CH$_2$)$_4$— or —(CH$_2$)$_5$—, R'' represents hydrogen, methyl or $C_{2-6}$ alkyl which is unsubstituted or substituted by $C_{1-4}$ alkoxy or $C_{4-6}$ alkoxyalkoxy or, together with R', represents —(CH$_2$)$_4$— or —(CH$_2$)$_5$—, R''' represents methyl, $C_{2-6}$ alkyl which is unsubstituted or substituted by $C_{1-4}$ alkoxy or $C_{3-6}$ alkoxyalkoxy, cyclohexyl which is unsubstituted or substituted by methyl and/or ethyl, or a radical of the formula

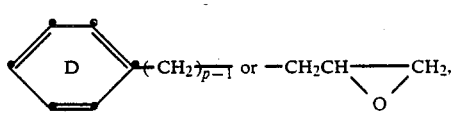

m represents the number 1 or 2 and n and p independently of one another represent the number 1, 2 or 3, it being possible for the rings A, B and D to be monosubstituted or disubstituted by $C_{1-3}$ alkyl and/or halogen, and, if n and p each represent the number 1, for the rings B and D to be trisubstituted by $C_{1-3}$ alkyl and/or halogen or to be monosubstituted or disubstituted by $C_{1-3}$ alkoxy.

4. A compound of claim 1, in which X represents bromine, $R_1$ represents hydrogen or $C_{1-4}$ alkyl, $R_2$ represents $C_{2-4}$ alkenyl, —CN, —CONR'R'', —COOR''' or —CO—R and $R_3$ represents hydrogen, $C_{1-4}$ alkyl or —CH$_2$COO—$C_{1-4}$ alkyl, R represents methyl, $C_{2-6}$ alkyl which is unsubstituted or substituted by $C_{1-4}$ alkoxy or $C_{4-6}$ alkoxyalkoxy, or naphthyl or represents phenyl which is unsubstituted or substituted by halogen, $C_{1-33}$ alkyl and/or $C_{1-3}$ alkoxy, R' and R'' each represent methyl or ethyl or together represent —(CH$_2$)$_4$— or —(CH$_2$)$_5$—, R''' represents methyl or $C_{2-6}$ alkyl which is unsubstituted or substituted by $C_{1-4}$ alkoxy or $C_{3-6}$ alkoxyalkoxy, m represents the number 1, and n and p independently of one another represent the number 2 and, in particular, the number 1.

5. A compound of claim 1, in which X represents bromine, $R_1$ represents hydrogen or $C_{1-4}$ alkyl, $R_2$ represents $C_{2-4}$ alkenyl, —CN, —CONR'R'', —COOR''' or —CO—R and $R_3$ represents hydrogen, $C_{1-4}$ alkyl or —CH$_2$COO—$C_{1-4}$ alkyl, at least one of $R_1$ and $R_3$ represents hydrogen, R represents $C_{1-6}$ alkyl or phenyl which is unsubstituted or substituted by halogen, $C_{1-3}$ alkyl or $C_{1-3}$ alkoxy, in particular unsubstituted $C_{1-4}$ alkyl or phenyl which is unsubstituted or monosubstituted by chlorine, methyl or methoxy, R' and R'' each represent methyl or ethyl or together represent —(CH$_2$)$_5$— and R''' represents methyl or $C_{2-6}$ alkyl which is unsubstituted or substituted by $C_{1-4}$ alkoxy or $C_{3-6}$ alkoxyalkoxy, in particular unsubstituted $C_{1-4}$ alkyl.

6. A compound of claim 1, in which X represents bromine, $R_1$ represents methyl or hydrogen, $R_2$ represents —CN,

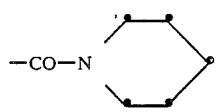
or —COOR''', R''' represents unsubstituted $C_{1-4}$ alkyl and $R_3$ represents hydrogen, methyl, —CH$_2$COOCH$_3$ or —CH$_2$COOC$_2$H$_5$, at least one of $R_1$ and $R_3$ representing hydrogen.
7. The compound of the formula
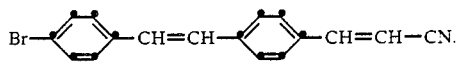
8. The compound of the formula
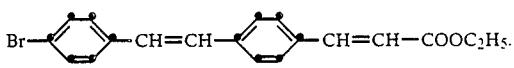
* * * * *